United States Patent [19]

Barrodale et al.

[11] Patent Number: 4,563,183

[45] Date of Patent: Jan. 7, 1986

[54] FEMALE EXTERNAL CATHETER

[76] Inventors: Patricia M. Barrodale, 2102 Dunstan St., Houston, Tex. 77005; Mary A. Young, 2419 Charriton Dr., Houston, Tex. 77039; Joan H. Humphreys, 402 Live Oak, Stafford, Tex. 77477; James M. Lowrey, Jr., 3815 Monterey Pl., Boulder, Colo. 80301

[21] Appl. No.: 482,583

[22] Filed: Apr. 6, 1983

[51] Int. Cl.⁴ ............................................. A61M 1/00
[52] U.S. Cl. .................................. 604/329; 604/355; 128/761
[58] Field of Search ............... 604/329, 330, 328, 327, 604/355, 344, 346, 171, 172, 280–282, 49, 317, 54, 55, 174, 180, 278, 279; 128/761

[56] References Cited

U.S. PATENT DOCUMENTS

| 3,194,238 | 7/1965 | Breece, Jr. | 128/295 |
| 3,292,626 | 12/1966 | Schneider | 128/295 |
| 3,374,790 | 3/1968 | Mayhorne | 128/295 |
| 3,556,102 | 1/1971 | Davis | 128/295 |
| 3,601,125 | 8/1971 | Moss | 128/295 |
| 3,613,122 | 10/1971 | Gross et al. | 128/267 |
| 3,683,914 | 8/1972 | Crowley | 604/329 |
| 3,776,235 | 12/1973 | Ratcliffe et al. | 128/295 |
| 3,854,483 | 12/1974 | Powers | 604/172 |
| 4,198,979 | 4/1980 | Codney et al. | 128/295 |
| 4,233,978 | 11/1980 | Hickey | 128/295 |
| 4,270,539 | 6/1981 | Michaud | 128/295 |

FOREIGN PATENT DOCUMENTS

| 2090741 | 7/1982 | United Kingdom . | |
| 542519 | 1/1977 | U.S.S.R. | 604/280 |

Primary Examiner—Michael H. Thaler
Attorney, Agent, or Firm—Hubbard, Thurman, Turner & Tucker

[57] ABSTRACT

Disclosed is a female external catheter which includes an intralabial flange with an adhesive body on one side and an outwardly extending urinary tube on the other side. The adhesive body is adapted to adhere to and seal with the tissue of the vestibule of a female patient around the urethral meatus and vaginal introitus and occlude the introitus. The urinary tube has a bore that extends through the flange and adhesive body to surround the urethral meatus and isolate it from the introitus. A vent is provided for venting the vagina.

23 Claims, 6 Drawing Figures

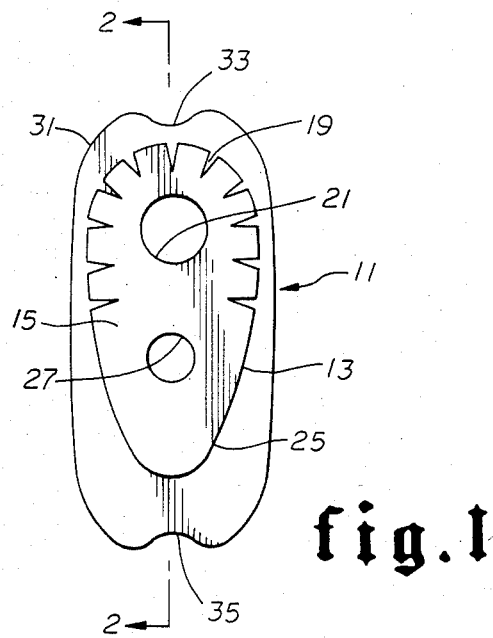
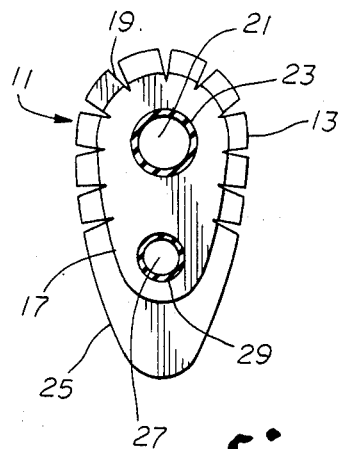
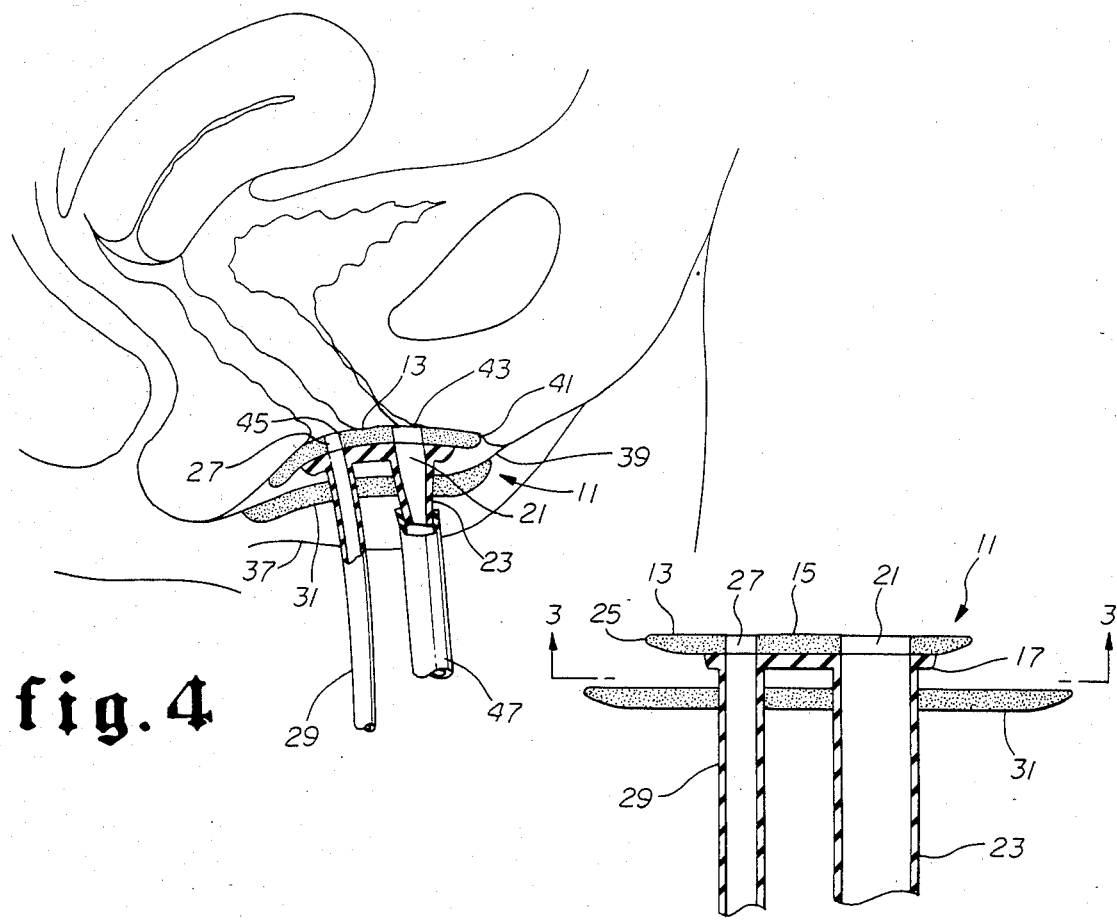

FEMALE EXTERNAL CATHETER

BACKGROUND OF THE INVENTION

1. Field of the Invention

The present invention relates generally to urine collection devices and more particularly to a non-invasive female external urine collection device or catheter.

2. Description of the Prior Art

Hospitalized patients who are unable to control their urinary functions, or who, while being able to control their urinary functions, are unable physically to use a urinal or bed pan, are fitted with urine collection devices known as catheters. Male patients are provided with indwelling catheters only so long as urine volumes need to be monitored hour-to-hour, after which time they are switched to external catheters. Women, on the other hand, keep indwelling catheters as long as they remain unable to use normal facilities and frequently develop severe bladder infections.

While some non-hospitalized incontinent women wear indwelling catheters and take antibiotics for their bladder infections, others wear absorbent pads or diaper-like garments to soak up urine. However, in addition to being generally uncomfortable and of limited absorbent capacity, prolonged contact of such urine soaked pads or garments with the skin leads to skin irritation and in some cases ulceration of the skin.

There have been developed heretofor a number of female external urinals or urine collection devices; however, none of such devices has been completely satisfactory. Examples of one class of device are disclosed in U.S. Pat. No. 4,233,978 and U.S. Pat. No. 3,601,125, which broadly provide a collection receptacle that is positioned exterior of and seals completely around the patient's vulva. The device of the U.S. Pat. No. 4,233,978 is attached to the patient by means of an adhesive rim, while the device of the U.S. Pat. No. 3,601,125 is attached to the patient by means of a belt and strap arrangement. A shortcoming of both devices is that when they are used on a reclining patient, urine flows toward and may collect in the vagina, thereby leading to vaginal inflammation.

A further shortcoming in the U.S. Pat. No. 3,601,125 is in the method of attachment to the patient and in the considerable external bulk located between the patient's legs. In an attempt to provide a seal, substantial pressure must be applied by the belts to the device of the U.S. Pat. No. 3,601,125, which pressure can be damaging to tissue. Also, the external bulk of the device of the U.S. Pat. No. 3,601,125 may be uncomfortable to the wearer and may cause chafing or other irritation to the wearer's legs.

Another class of female external urine collection devices includes devices which are adapted to be positioned interior of the labia of the patient. One example of such a device is disclosed in U.S. Pat. No. 3,776,235. The device of the U.S. Pat. No. 3,776,235 includes a generally funnel-like collection chamber that is positioned on the patient by an intravaginal projection. The intravaginal projection is hollow and provides a flow path for ventilation and the passage of fluids to and from the vagina. However, the flow path communicates with the collection chamber and thereby, when used on reclining patients, provides a pathway for the flow of urine into the vagina and creates a substantial posterior leak.

Another such device is disclosed in U.S. Pat. No. 4,198,979, which includes a generally funnel-shaped, rigid collection means having a wide orifice with a flange thereabout. The wide orifice is sized to encompass both the urethral and vaginal orifices and the flange has mounted thereon a layer of body adhesive that is adapted to form a seal with the vestibule of the wearer interior of the labia minora. The labia minora contacts the underside of the flange and the exterior of the collection means to urge the flange and adhesive sealant into a more intimate contact with the vestibule of the patient. The preferred embodiment of the device of the U.S. Pat. No. 4,198,979 includes a pommel or projection that is adapted for insertion into and contact with the posterior side of the vagina.

The device of the U.S. Pat. No. 4,198,979 provides for the communication of urine to the vagina. The communication would appear to be accentuated in the preferred embodiment which includes the pommel. Additionally, the wide orifice allows substantially the entire area of the vestibule to be contacted with urine. Also, the tension placed by the device on the labia minora could result in stretching or other tissue damage.

In U.S. Pat. No. 4,270,539, there is disclosed a urine collection device which includes an interface body that engages the vestibule of the patient interior of the labia minora. The interface body includes a forward portion having a urine receiving bore and a rearward portion having a non-invasive vaginal seal. An absorbent pad is positioned about the interface body to absorb urine leaks. The device is held firmly against the user by a garment.

The device of the U.S. Pat. No. 4,270,539 must be custom made so as to fit the sizes and relative positions of the vaginal and urethral orifices of the patient. In order to form an effective vaginal seal, the device must be firmly urged against the tissue of the wearer, which could lead to irritation or tissue damage. Moreover, the vaginal seal, while being non-invasive, is occlusive in that it provides no ventilation to the vagina. The urine receiving portion of the device is not substantially leak-proof and, indeed, a pad is provided for containing leaks.

A further female external urine collection device is disclosed in U.S. Pat. No. 3,613,122.

It is therefore an object of the present invention to provide a female external catheter that overcomes the shortcomings of the prior art. More specifically, it is an object of the present invention to provide a female external catheter that provides for the isolation of the urethral and vaginal openings but which is normally non-invasive of either the vagina or the urethra and which is non-occlusive of the vagina. It is a further object of the present invention to provide a female external catheter which provides for collection of substantially all urine passed by the patient, but which minimizes the amount of skin contacted by urine. It is a further object of the present invention to provide a female external catheter that is substantially universal in that one size and configuration fits substantially all women and need not be custom made. It is a further object of the present invention to provide a female external catheter that can be used effectively by walking, standing, seated, or reclining patients and which is of limited bulk and comfortable to the patient. It is a further object of the present invention to provide a female external catheter that is self supporting without pressure or substantial traction to the tissues and which may be worn without pads, belts, or supporting garments. It is a further object of the present invention to provide a female external catheter that is easy to apply and which may be self applied. It is yet a further object of the present invention to provide a female external catheter that is compatible with pre-existing drainage and collection devices. It is still another object of the present invention to provide a female external catheter that will allow a patient to "straight cath" herself without removing the device.

SUMMARY OF THE INVENTION

The foregoing and other objects are met by the present invention, which includes a substantially flat adhesive body carried by a flexible substantially flat substrate. The adhesive body is sized to fit within the labia minora of the patient and sealingly adhere to the tissue of the vestibule. The adhesive body is formed from a body adhesive of a sticky, wax-like material that has some tendency to melt and conform to the body at body temperature.

The adhesive body and the substrate each include a urinary bore sized to surround the urethral orifice and isolate the urethral orifice from the vaginal orifice. The substrate includes a urinary tube coaxial with the urinary bore, which provides a flow-way for urine away from the wearer. The adhesive body and substrate preferably also include a vent bore that is spaced apart from the urinary bore to vent the vaginal orifice or introitus. The substrate may include a vent tube coaxial with the vent bore and extending outwardly from the wearer.

The female external catheter of the present invention may also include an interlabial second adhesive body which surrounds the urinary and vent tubes and which is independently affixable to the external aspects of the labial minora. The interlabial adhesive body is preferably formed of a moldable body adhesive that has some tendency to melt and conform to the body temperature, similar to the intralabial adhesive body. The interlabial adhesive body conforms to the external aspects of the labia minora and provides support to the device.

BRIEF DESCRIPTION OF THE DRAWINGS

FIG. 1 is a top view of the female external catheter of the present invention.

FIG. 2 is a section view along line 2—2 of FIG. 1.

FIG. 3 is a section view along line 3—3 of FIG. 2.

FIG. 4 is a cross sectional view of a portion of a female human body showing the preferred embodiment of the present invention in place.

DESCRIPTION OF THE PREFERRED EMBODIMENT

Figure 5:
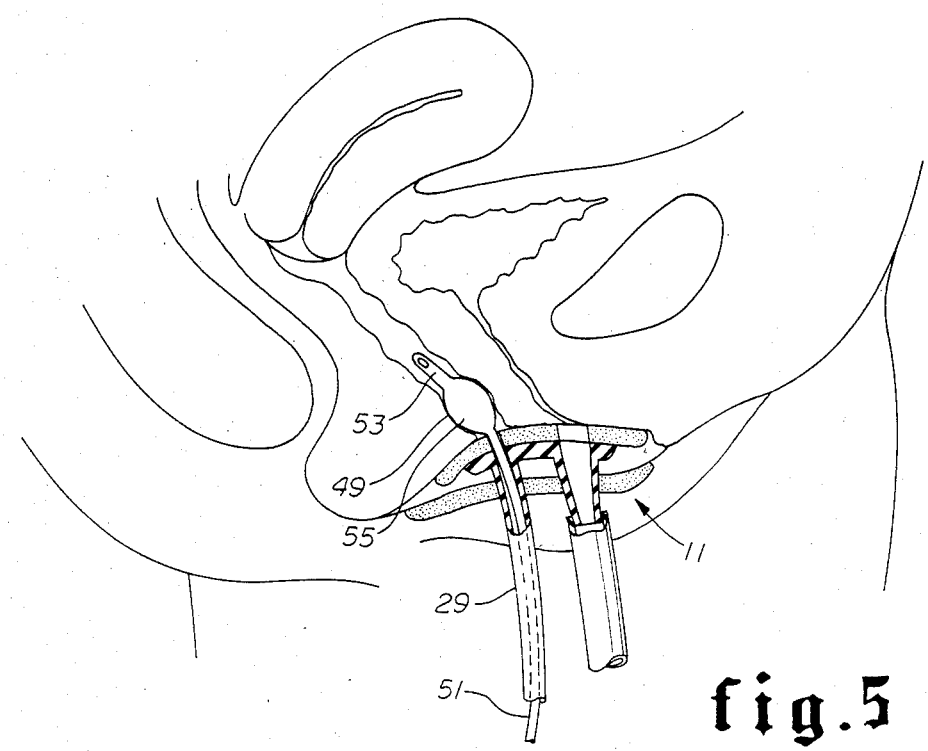
FIG. 5 is a cross sectional view of a portion of a female human body showing an alternative embodiment of the present invention.

Referring now to the drawings, and first to FIG. 1-3, the female external catheter of the present invention is designated generally by the numeral 11. Catheter 11 includes a generally oval substantially flat, intralabial adhesive body 13, which is shaped and sized to fit within the vestibule of a female patient interior of the labia minora. Intralabial adhesive body 13 includes a sticky adhesive surface 15 which is adapted to removably sealingly adhere to the skin of the vestibule of the patient. Intralabial adhesive body 13 is flexible and preferably moldable so as to conform to the contours and irregularities of the vestibule and is preferably formed of a layer of body adhesive. Such body adhesives are well known in the art and are commercially available in sheets which have a wax-or-putty-like appearance and consistency. The preferred body adhesive materials of intralabial adhesive body 13 have some tendency to melt and conform to the contours of the body at body temperature and form a substantially leakproof seal with skin that is substantially impervious to urine. The body adhesive material should be chosen so as not to produce allergic or other adverse effects to the patient. The most preferred body adhesive for the practice of the present invention is manufactured by the Hollister Company and marketed under the trademark "HOLLIHESIVE".

Intralabial adhesive body 13 is supported on a substantially flat substrait, which in the preferred embodiment is a flange 17. Flange 17 is formed of a biomedical grade plastic and is preferably flexible so as to conform to the contours of the vestibule. The flexibility and conformability to curved surfaces of intralabial adhesive body 13 and flange 17 may be improved by the inclusion of a plurality of radial slits 19 about the respective peripheries thereof. Also, since intralabial adhesive body 13 is inherently more flexible than flange 17, intralabial adhesive body extends outwardly of flange 17.

Intralabial adhesive body 13 and flange 17 include at their anterior end a urinary bore 21. Urinary bore 21 is sized to encircle the urethral orifice or meatus of the patient while isolating the urethral orifice or meatus from the vaginal orifice or introitus. Flange 17 includes a urinary tube 23 that extends outwardly from flange 17 coaxial with urinary bore 21.

While the size of the vaginal introitus and its distance from the urethral meatus vary considerably from patient to patient, the introitus is always generally posterior to the urethral meatus. Accordingly, the posterior portion 25 of intralabial adhesive body 13 is made long enough to extend posteriorly far enough to occlude the introitus of patients. There is sufficient tissue between the introitus and the urethral meatus for intralabial adhesive body to form a substantially leakproof seal therebetween. However, in order to prevent intralabial adhesive body 13 from completely occluding the introitus, a vent bore 27 is provided in intralabial adhesive body 13 and flange 17 of the preferred embodiment. Vent bore 27 is spaced posteriorly apart from urinary bore 21 so as to coincide in substantially all patients with some portion of the introitus. Flange 17 may include an outwardly extending vent tube 29 coaxial with vent bore 27. Vent bore 27 allows both the ventilation of the vagina and provides a flow way for the passage of menses or other discharges.

The preferred embodiment of external catheter 11 also includes an interlabial adhesive body 31. Interlabial adhesive body is positioned outwardly of flange 17 and about urinary tube 23 and vent tube 29. Interlabial adhesive body 31 is initially slidable on urinary tube 23 and vent tube 29 so as to be movable into intimate contact with the external aspects of the labia minora of the patient. Interlabial adhesive body 31 is preferably formed of a body adhesive material similar or identical to that of intralabial adhesive body 23. Accordingly, when interlabial adhesive body 31 is moved into intimate contact with the body of the patient, it has a tendency to melt somewhat and conform and adhere to both the patient and to urinary tube 23 and vent tube 29. Interlabial adhesive body 31 thus provides a secondary or backup seal to that formed by intralabial adhesive body 13 and provides structural support to external catheter 11, thereby making it self supporting without the need for belts or other supporting garments.

Interlabial adhesive body 31 may include an anterior notch 33 so that interlabial adhesive body 31 does not interfer with the clitoris of the patient. Similarly, interlabial adhesive body 31 may include a posterior notch 35 so as not to interfere with the anus.

Referring now to FIG. 4, the preferred external catheter 11 is shown positioned upon a patient. External catheter 11 is applied to the patient by first retracting or spreading both the labia majora 37 and minora 39 thereby to expose the vestibule 41. External catheter 11 is then placed in the vestibule with urinary bore 21 about the urethral meatus 43 and vent bore 27 coinciding generally with introitus 45. External catheter 11 is then held firmly in place for about a minute to allow intralabial adhesive body 13 to conform and adhere to vestibule 41. The labia minora 39 are then allowed to close over the intralabial adhesive body 13 and flange 17, whereupon interlabial adhesive body 31 is moved into intimate contact with the external aspects of labia minora 39. Interlabial adhesive body 31 then melts to conform and adhere to labia minora 39 and a portion of the outer surface of flange 17 and tubes 23 and 29. After interlabial adhesive body has been so placed, labia majora 37 are allowed to close over the interlabial adhesive body.

With external catheter 11 so mounted, the only external projections are urinary tube 23 and vent tube 29. External catheter 11 thus provides a minimum of external bulk and thereby reduces irritation to and increases mobility of the patient. Urinary tube 23 may be connected by a drainage tube 47 to any commonly available drainage or collection device, as for example, a leg bag.

Referring now to FIG. 5, there is shown an alternative embodiment of the present invention, which includes an invasive vaginal seal. The invasive vaginal seal is provided by a so-called Foley catheter 49 which is inserted into the vagina through vent bore 27. The structure and operation of Foley catheter is generally well known. In general, Foley catheter 49 includes a tube 51 having an inlet 53 at the upper end thereof. An inflatable bladder 55 is positioned about tube 51. Foley catheter 49 is inserted into the introitus through vent tube 29 with bladder 55 uninflated. When Foley catheter 49 is properly positioned within the vagina, bladder 55 is inflated, thereby to provide an invasive seal. The vagina remains vented through inlet 53 of tube 51.

Figure 6:
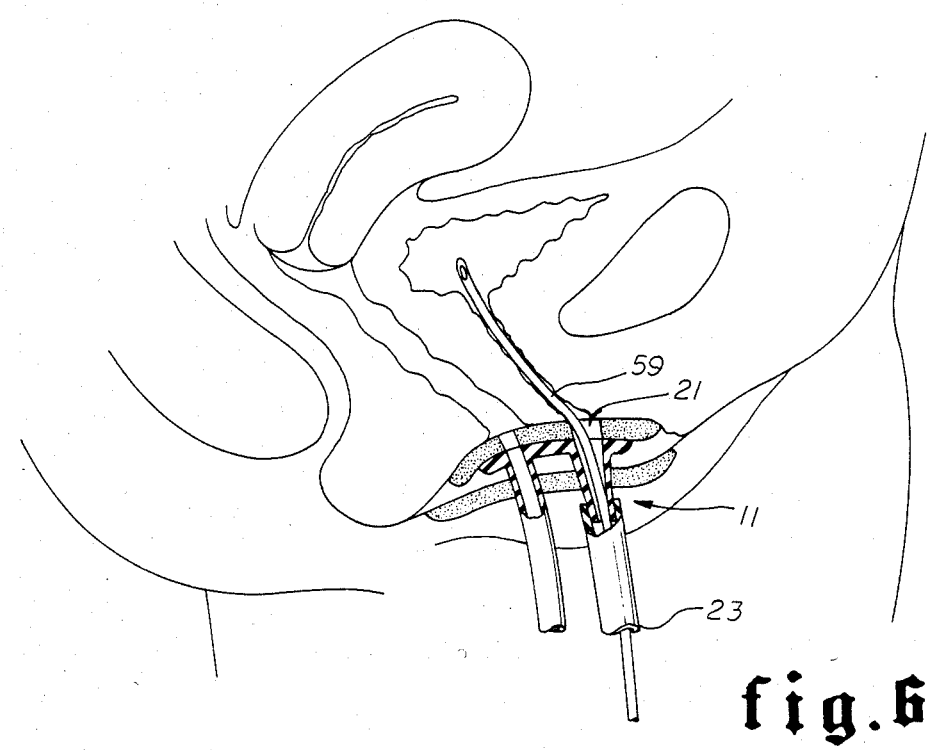
FIG. 6 is a cross sectional view of a portion of a female human body showing the method of placing an indwelling catheter through the device of the present invention.

External catheter 11 is readily self appliable and is therefore useful to incontinent out-patients. External catheter 11 is particularly useful to incontinent out-patients who, while uncontrollably passing small amounts of urine, find it necessary periodically to use an indwelling catheter to achieve substantially complete drainage of urine. As shown in FIG. 6, such patients, having applied external catheter 11 in the manner described above and a local skin prep to the inside of urinary tube 23 and the skin therewithin, may insert a "straight cath" 59 through urinary tube 23 and urinary bore 21 into the urethra and the bladder. Urinary tube 23 thus provides a pilot or guide for the straight cath, thus making it easier for the patient to self catheterize herself.

From the foregoing it will be seen that this invention is one well adapted to attain all of the ends and objects hereinabove set forth, together with other advantages which are obvious and which are inherent to the apparatus.

It will be understood that certain features and subcombinations are of utility and may be employed with reference to other features and subcombinations. This is contemplated by and is within the scope of the claims.

As many possible embodiments may be made of the invention without departing from the scope thereof, it is to be understood that all matter herein set forth or shown in the accompany drawings is to be interpreted as illustrative and not in a limiting sense.

What is claimed:

1. A female external catheter, which comprises:
   an intralabial flange having a urinary bore sized to surround the urethral opening of a female user, said intralabial flange having opposed inwardly and outwardly facing sides;
   a urinary tube connected to and extending outwardly from said outwardly facing side of said intralabial flange coaxial with said urinary bore;
   an intralabial first adhesive body mounted to said inwardly facing side of said intralabial flange having a bore coincident with said urinary bore of said intralabial flange, said intralabial first adhesive body being adapted to adhere to the skin of said female user around urethral opening interior to the labia minora and form a substantially leakproof seal about the urethral opening and isolate the urethral opening from the vaginal opening; and
   an interlabial second adhesive body positioned outwardly of said intralabial flange about said urethral tube, said interlabial second adhesive body being adapted for positioning interior to the labia majora to adhere to the external aspects of the labia minora of the female user to hold the labia minor together and against the intralabial flange, thereby to support the intralabial flange and intralabial first adhesive body.

2. The female external catheter as claimed in claim 1, wherein said intralabial adhesive body includes a sheet of material having a sticky surface and being moldable to conform to the contours of the tissue in the vestibule of the female user.

3. The female external catheter as claimed in claim 1, wherein said intralabial flange is conformable to fit the contours of the vestibule of the female user.

4. The female external catheter as claimed in claim 1, wherein said intralabial flange and intralabial adhesive body include a plurality of radial peripheral slits for allowing said intralabial flange and adhesive body to conform to the contours of the vestibule of the female user.

5. The female external catheter as claimed in claim 1, wherein said intralabial flange is flat and said urinary tube has substantially the same inside diameter as said urinary bore.

6. The female external catheter as claimed in claim 1, including means for venting the vaginal opening.

7. The female external catheter as claimed in claim 6, wherein said means for venting includes coincidental vent openings in said intralabial flange and said intralabial adhesive body, said vent openings being spaced apart from said urinary bore to substantially coincide with the vagina of the female user.

8. The female external catheter of claim 7, wherein the vent opening of said intralabial flange is a vent bore, and wherein said female external catheter further includes a vent tube connected to and extending outwardly from said outwardly facing side of said intralabial flange coaxial with the vent bore of said intralabial flange.

9. A female external catheter, which comprises:

a urinary tube having a bore sized to surround the urethral opening of a female user and including an outwardly extending flange sized to fit within the vestibule interior of the labia minora of a female user;

adhesive means for forming a substantially leakproof seal between said flange and the skin of the female user around the urethral opening of the female user interior of the labia minora and isolating the urethral opening from the vaginal opening; and an interlabial adhesive sheet positioned outwardly of said flange about said urinary tube and adapted for positioning interior of the labia majora to adhere to the external aspect of the labia minora of the female user to hold the labia minora together and against the outwardly extending flange, thereby to support the outwardly extending flange.

10. The female external catheter as claimed in claim 9, wherein said flange includes a vent opening spaced apart from said urethral bore to provide ventilation to the vaginal opening of the female user.

11. The female external catheter as claimed in claim 10, wherein said vent opening of said flange is a vent bore;

wherein said female external catheter includes a vent tube connected to and extending from said flange in communication with said vent bore; and wherein said interlabial adhesive sheet is also positioned about said vent tube.

12. The female external catheter as claimed in claim 9, wherein said substantially leakproof seal forming means includes a sheet of adhesive material applied to said flange surrounding said urinary bore.

13. The female external catheter as claimed in claim 12, wherein said sheet of adhesive material is conformable to the contours of the tissue of the vestibule of the female user.

14. The female external catheter as claimed in claim 9, wherein said flange is substantially flat.

15. The female external catheter as claimed in claim 14, wherein said flange is flexible.

16. The female external catheter as claimed in claim 9, wherein said urinary tube and urinary bore have substantially the same inside diameter.

17. The female external catheter as claimed in claim 9, including means for venting the vagina of the female user.

18. The female external catheter as claimed in claim 17, wherein said venting means includes:

vent bores formed in said flange and in said interlabial adhesive sheet;

a vaginal tube extending through said vent bore;

and an inflatable bladder positioned about said vaginal tube interior of said flange.

19. A female external catheter, which comprises:

an adhesive body carried by a substrate, said adhesive body being conformingly sealingly adhereable to the tissue of the vestibule of a female user about and between the urethral meatus and the vaginal introitus of the female user, said adhesive body and substrate including a urinary bore sized to surround the urethral meatus and isolate the urethral meatus from the vaginal introitus;

a urinary tube connected to and extending outwardly from said substrate in communication with said urinary bore; and an interlabial adhesive body positioned outwardly of said substrate about said urinary tube and adapted for positioning interior of the labia majora to adhere to the external aspect of the labia minora of the female user to hold the labia minora together and against the substrate, thereby to support the substrate.

20. The female external catheter as claimed in claim 19 including a vent opening defined in said adhesive body and substrate spaced apart from said urinary bore.

21. The female external catheter as claimed in claim 20, including:

a vent tube connected to and extending outwardly from said substrate in communication with said vent opening.

22. A female external catheter, which comprises:

a urinary tube;

means for adhering an end of said urinary tube to the tissue of the vestibule of a female user;

and an interlabial adhesive body positioned about said urinary tube and adapted for positioning interior of the labia majora to adhere to the external aspect of the labia minora of the female user to hold the labia minora together to support said urinary tube.

23. The female external catheter as claimed in claim 22, wherein said means for adhering includes:

a flange extending radially outwardly from said end of said urinary tube;

and an intralabial adhesive body affixed to said flange surrounding said end of said urinary tube.

* * * * *